United States Patent

Shimizu et al.

[11] Patent Number: 5,756,836
[45] Date of Patent: May 26, 1998

[54] PROCESS FOR PRODUCING HIGHLY PURIFIED ACETIC ACID

[75] Inventors: Masahiko Shimizu; Kazuyuki Akita; Yasuteru Kajikawa; Takashi Ueno; Yasuo Tsuji; Yoshiaki Morimoto, all of Hyogo, Japan

[73] Assignee: Daicel Chemical Industries, Ltd., Osaka, Japan

[21] Appl. No.: 591,947

[22] Filed: Jan. 23, 1996

Related U.S. Application Data

[63] Continuation of Ser. No. 254,934, Jun. 7, 1994, abandoned.

[30] Foreign Application Priority Data

Jul. 8, 1993 [JP] Japan .................. 5-169204
Jul. 8, 1993 [JP] Japan .................. 5-169205

[51] Int. Cl.$^6$ .................. C07C 51/12; C07C 51/42
[52] U.S. Cl. .................. 562/519; 562/608
[58] Field of Search .................. 562/519, 608

[56] References Cited

U.S. PATENT DOCUMENTS 5,155,266 10/1992 Scates et al. .................. 562/608
5,206,434 4/1993 Scates et al. .................. 562/891

*Primary Examiner*—Gary Geist
*Assistant Examiner*—Rosalynd Keys
*Attorney, Agent, or Firm*—Flynn, Thiel, Boutell & Tanis, P.C.

[57] ABSTRACT

The present invention relates to a process for producing a highly purified acetic acid characterized in that in the process for producing acetic acid comprising the step of continuously reacting methanol and/or an aqueous solution of methyl acetate with carbon monoxide in a reactor, a treatment is conducted to limit the concentration of unsaturated compounds in crude acetic acid obtained in the process to 5 ppm or lower, and the resultant crude acetic acid is ozonized. The present invention also relates to a process for producing a highly purified acetic acid, characterized by comprising the step of continuously reacting methanol and/or an aqueous solution of methyl acetate with carbon monoxide in a reactor while maintaining the concentration of acetaldehyde in a reaction fluid in the reactor at 1500 ppm or lower.

11 Claims, 1 Drawing Sheet

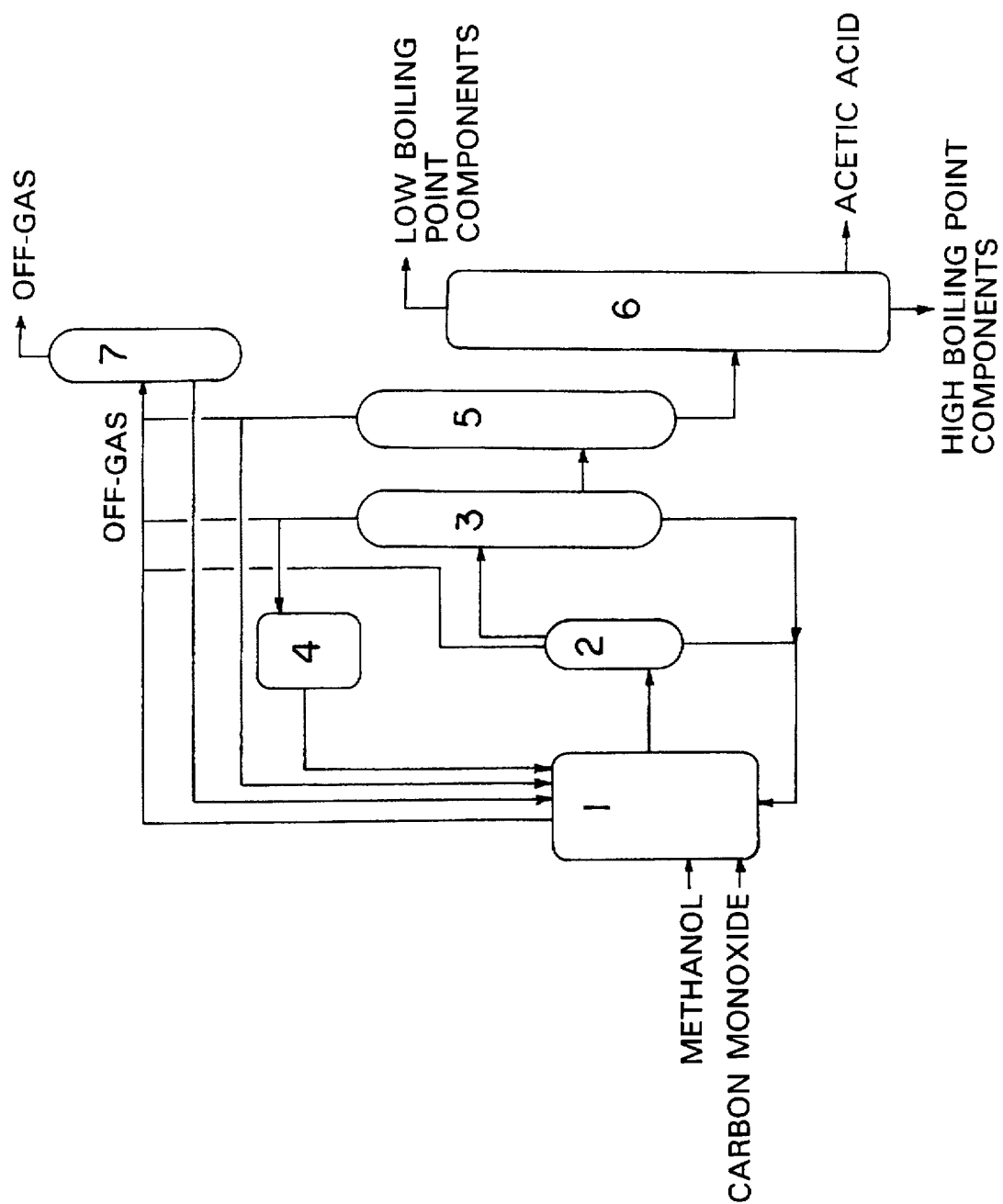

PROCESS FOR PRODUCING HIGHLY PURIFIED ACETIC ACID

This application is a continuation of U.S. Ser. 08/254,934, filed Jun. 7, 1994, abandoned.

BACKGROUND OF THE INVENTION

1. Technical Field

The present invention relates to an industrial process for producing a highly purified acetic acid. The present invention is concerned with, specially, a process for continuously producing an acetic acid having a lowered content of reducing impurities.

2. Description of the Related Art

Acetic acid is a basic chemical which is used in large quantity in the petrochemical industry, organic chemical industry, pharmaceutical and agricultural chemical producing industry, polymer chemical industry and the like.

Various industrial processes are known for producing acetic acid. Among them, the process which comprises continuously reacting methanol with carbon monoxide to thereby produce acetic acid [see Herbert D. Grove, Hydrocarbon Process No. 11, 76 (1972) and Japanese Patent Publication-B No. 47-3334] is the most industrially advantageous one. According to this process, not only is the production of acetic acid high, but also the production of by-product impurities is reduced. Therefore, when acetic acid is produced by this process, acetic acid having a purity higher than those of the acetic acids produced by other processes can be obtained.

However, even if the above process is adopted, trace impurities as a by-product is produced. Accordingly, when continuous operation is performed for a prolonged period of time, even though acetic acid is produced according to the above process, by-product impurities contaminate acetic acid as the target product to thereby cause the quality of the product to be poor. Therefore, even if the above process is adopted, large facilities are used and much energy is consumed for purification of acetic acid.

In recent years, as industrial process for producing acetic acid at a high productivity, a process with respect to the improvement of the catalyst for the production of acetic acid which comprises a catalyst stabilizer, such as iodide salts, is added and another process in which methanol is reacted with carbon monoxide under such a condition such that the water content is lower than that of the prior art have been proposed [see U.S. Pat. No. 5214203 (assignee: Daicel Chemical Industries Co. Ltd., patented date: May 25, 1993) and U.S. Pat. No. 5,001,259 (assignee: Hoechst Celanese Corp., patented date: Mar. 19, 1991)]. It is stated that the amounts of by-products, such as carbon dioxide and propionic acid, are reduced when any of such processes is employed alone or these employed in combination. However, as to some impurities produced as by-products in trace amounts, other than carbon dioxide and propionic acid, the amounts thereof increase in accordance with an increase in the productivity of acetic acid. Therefore, when the productivity of acetic acid is enhanced by the above catalyst improvement or changes of reaction conditions, it is likely that the amounts of impurities other than carbon dioxide and propionic acid will increase to thereby cause the quality of the acetic acid to be poor.

A quality test, called the permanganate reducing substance test (permanganate time), for checking the amounts of reducing impurities present in acetic acid, even in trace amounts, permits the detection of a slight increase in the amounts of trace impurities, the determination of which is difficult, even by analysis with modern high-performance instruments. Therefore, this test has demonstrated the lowering of the quality of acetic acid by these reducing impurities. In the art, an acetic acid exhibiting a permanganate time of generally 120 min or longer, preferably 240 min or longer, is recognized as being excellent in quality. Examples of such impurities include aldehydes, especially unsaturated aldehydes. Although the aldehydes include a variety of compounds, individual separation and removal thereof from crude acetic acid is not practical. In particular, crotonaldehyde, 2-ethylcrotonaldehyde and the like, which are condensates of acetaldehydes through dehydration, have boiling points close to that of acetic acid, so that it is difficult to separate such trace impurities from acetic acid by distillation.

As processes for purifying acetic acid, those wherein crude acetic acid containing trace reducing impurities as mentioned above is treated with ozone [see Japanese Patent Publication-B No. 61-2052 (published on Jan. 22, 1986)] or with an oxidizing agent have been disclosed. However, the treatment of crude acetic acid with ozone or an oxidizing agent has a drawback in that the concentrations and types of the impurities which can be treated are limited. For example, with respect to the treatment with ozone, there are drawbacks that (1) only unsaturated compounds can be treated with ozone, while saturated aldehydes cannot be decomposed by the treatment with ozone and that (2) the decomposition products resulting from the treatment of unsaturated compounds with ozone are saturated aldehydes, which also have reducing power, so that they are nothing but compounds, which are worse in the permanganate time. Therefore, for removing the saturated aldehydes after the treatment of crude acetic acid with ozone, purification procedures, such as treatment with active carbon, are further required [see European Patent No. 322215 (published on Jun. 28, 1989)].

DISCLOSURE OF THE INVENTION

SUMMARY OF THE INVENTION

The present inventors have accomplished detailed identification of reducing impurities which lower the quality of acetic acid, and have made fully an examination of the route of occurrence of the impurity compounds. As a result, they have found that acetaldehyde formed during the reaction is a fundamental causal substance of such trace reducing impurities.

In the conventional process for producing acetic acid, components contained in a reaction fluid and having boiling points lower than that of acetic acid, such as methyl acetate derived from methanol as a starting compound, methyl iodide as a promoter and water present in the reaction fluid, are separated from acetic acid in the course of separation of acetic acid from a crude reaction fluid. However, most of the separated compounds are recycled to the reactor in order to avoid the wasting thereof. That is, these compounds are circulated in the process for producing acetic acid and reutilized. Accordingly, by-product acetaldehyde formed in trace amount by the reaction in the reactor is circulated in the process without being removed. Therefore, during the reaction, acetaldehyde is accumlated in the reaction fluid.

The accumulated acetaldehydes are condensed under reaction conditions for the synthesis of acetic acid to form unsaturated aldehydes such as aldehydes having an alkenyl group. The formed acetaldehydes are reduced by hydrogen present under reaction conditions for the synthesis of acetic acid to also form propionic acid. Propionic acid has a boiling point higher than that of acetic acid, so that, after being withdrawn together with acetic acid from the reaction system, it is separated as a high boiling point fraction from acetic acid in a distillation column for purifying acetic acid by distillation in the step of separating acetic acid from the reaction fluid, and thus removed from the process. Accordingly, the acetaldehyde produced by the reaction in the reactor is removed from the process by any means capable of separating propionic acid from the process, contaminating acetic acid in the form of a condensate from the system, or distilled out from the system as a low boiling point fraction.

In the purification step for acetic acid, it is difficult to separate unsaturated aldehydes formed by the condensation of acetaldehydes and having a high boiling point, namely, boiling point close to that of acetic acid, among the substances derived from acetaldehyde. Therefore, the unsaturated aldehydes contaminate acetic acid as impurities to thereby lower the quality of acetic acid, that is, to impair the results of the reducing substance test for acetic acid.

Therefore, the amount of the reducing substances contaminating acetic acid can be decreased by separating and removing acetaldehyde accumulated in the reaction fluid from the low boiling point fraction being circulatingly used.

On the other hand, ozonization is effective in decreasing the amount of the reducing impurities present in the crude acetic acid, as mentioned hereinbefore. However, when the amount of the reducing impurities present in the crude acetic acid exceeds a certain level, mere ozonization is not effective in increasing the purity of acetic acid to such an extent that desired results are obtained in the reducing substance test. For obtaining an acetic acid capable of exhibiting desirable results in the reducing substance test, distillation and/or treatment with active carbon must be effected additionally after ozonization. The distillation in this case is to distill a large amount of acetic acid as the target product, so that enormous equipment and energy are required.

The above has led us to the conclusion that a highly purified acetic acid can be most economically produced by performing distillation of a low boiling point fraction of a small quantity to thereby remove acetaldehyde therefrom in combination with ozonization of crude acetic acid, and that, in other words, for producing a highly purified acetic acid, it is most effective and efficient to decrease the concentration of acetaldehyde in the circulating process fluid to such a level that a highly purified acetic acid having a reduced content of the reducing substances (a longer permanganate time) can be obtained only by ozonization. Based on this conclusion, the present invention has been completed.

Thus, the first embodiment of the present invention relates to a process for producing a highly purified acetic acid characterized in that in the process for producing acetic acid comprising the step of continuously reacting methanol and/ or an aqueous solution of methyl acetate with carbon monoxide in a reactor, a treatment is conducted to limit the concentration of unsaturated compounds in crude acetic acid obtained in the process to 5 ppm or lower, and the resultant crude acetic acid is ozonized.

Preferably, the treatment for limiting the concentration of unsaturated compounds in crude acetic acid obtained in the producing process to 5 ppm or lower is one for removing acetaldehyde from at least one process fluid separated in each step of the process for producing acetic acid and recycled to the reactor. As the treatment for removing acetaldehyde, distillation and/or extraction of the process fluid, and extractive distillation of the process fluid can be mentioned.

In the process of the present invention, further, it is preferred that a rhodium compound and methyl iodide be used as a catalyst and a promoter, respectively.

Accordingly, the first embodiment of the present invention includes a process for producing acetic acid comprising continuously reacting methanol and/or an aqueous solution of methyl acetate with carbon monoxide with the use of a rhodium complex and methyl iodide as a catalyst and a promoter, respectively, the concentration of unsaturated compounds in the obtained crude acetic acid is to be 5 ppm or lower, and further, the resultant crude acetic acid is ozonized to thereby produce acetic acid of high quality having a reduced content of reducing substances.

In this process, it is preferred that acetaldehyde, being the cause of the occurrence of impurities which are detrimental to the quality of acetic acid, be removed from the process fluid recycled to the reactor, so that the-concentration of unsaturated compounds in the obtained crude acetic acid is 5 ppm or lower.

Moreover, from the above chemical analysis, the present inventors have found that the amounts of impurities derived from acetaldehyde, i.e., propionic acid, to be formed, and unsaturated compounds which are detrimental to the quality of acetic acid, such as crotonaldehyde and 2-ethylcrotonaldehyde, to be formed, can be put under control by limiting the concentration of acetaldehyde in the reaction fluid in the reactor to 1500 ppm or lower, so that acetic acid of high quality can be produced without any need of enormous equipment or energy for removing each of the above impurity compounds from acetic acid. This finding has led to the completion of the present invention.

Thus, the second embodiment of the present invention relates to a process for producing a highly purified acetic acid, characterized by comprising the step of continuously reacting methanol and/or an aqueous solution of methyl acetate with carbon monoxide in a reactor while maintaining the concentration of acetaldehyde in a reaction fluid in the reactor at 1500 ppm or lower.

Preferably, removal of removing acetaldehyde from at least one process fluid separated in each step of the process for producing acetic acid and recycled to the reactor is conducted for maintaining the concentration of acetaldehyde in a reaction fluid in the reactor at 1500 ppm or lower. As the treatment for removing acetaldehyde, distillation and/or extraction of the process fluid, and extractive distillation of the process fluid can be mentioned.

In the process of the present invention, further, it is preferred that a rhodium compound and methyl iodide be used as a catalyst and a promoter, respectively.

Accordingly, the second embodiment of the present invention includes a process for producing highly purified acetic acid characterized in that in the process for producing acetic acid comprising continuously reacting methanol and/ or an aqueous solution of methyl acetate with carbon monoxide with the use of a rhodium complex and methyl iodide as a catalyst and a promoter, respectively, the reaction is conducted while maintaining the concentration of acetaldehyde in a reaction fluid at 1500 ppm or lower by separating acetaldehyde from the process fluid recycled to the reactor.

BRIEF DESCRIPTION OF THE DRAWING

FIG. 1 is a flow diagram illustrating a process for continuously producing acetic acid.

In FIG. 1, numeral 1 designates a reactor, numeral 2 represents an evaporator, numerals 3, 5 and 6 each represents a distillation column, numeral 4 represents a liquid separator and numeral 7 represents an absorption system.

The scope and applicability of the present invention will become apparent from the following detailed description. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The process of the present invention can be practiced by improving any of the conventional processes, for example, the Monsanto process. First, referring to FIG. 1, the Monsanto process will be described.

The process for continuously producing acetic acid from methanol and carbon monoxide as starting compounds was disclosed by Monsanto Company.

Methanol and carbon monoxide as starting compounds are continuously fed into a reactor (1), and continuously reacted at a given temperature under a given pressure. Generally, the reaction is effected under a temperature in the range of 150° to 250° C. and a pressure in the range of 15 to 40 atm. Further, in the reactor (1), a catalyst, a promoter, a solvent, a reaction accelerator, etc., are also added in addition to the above starting compounds, generally.

The catalyst is not particularly limited as long as it is soluble in a reaction fluid (reaction mixture) comprising the above starting compounds, etc., and reaction products under reaction conditions. The catalyst includes rhodium compounds, palladium compounds, palladium complexes, molybdenum compounds, nickel compounds and the like. Further, compounds comprising at least one compound selected from the group consisting of cobalt, iridium, platinum, osmium and ruthenium may also be used as the catalyst. As the catalyst, only one compound or two or more compounds may be used. When a rhodium compound is used as the catalyst, it is generally selected from those which are soluble in the reaction fluid and can form rhodium carbonyl species.

Examples of the rhodium compounds suitable for use in the present invention include:

$RhX_3$ (wherein X represents Cl, Br or I), $RhX_3 \cdot 3H_2O$ (wherein X represents Cl or Br), $Rh_2(CO)_{16}$, $Rh_2(CO)_5$, $Rh_2(CO)_4X_2$ (wherein X represents Cl, Br or I), $Rh(CO)X[(C_6H_5)_3M]_2$ (wherein X represents Cl, Br or I, and M represents P, As or Sb), $Rh(CO)_2X[(C_6H_5)_3M]$ (wherein X represents Cl, Br or I, and M represents P, As or Sb), $RhCl[(C_6H_5)_3P]_2(CH_3I)_2$, $Rh(SnCl_3)[(C_6H_5)_3P]_3$, $RhX[(C_6H_5)_3P]_3$ (wherein X represents Cl, Br or I), $RhCl[(C_6H_5)_3P]_3H_2$, $Rh[(C_6H_5)_3P]_2(CO)I$, $HRh(CO)[(C_6H_5)_3P]_3$, $[(C_6H_5)P]_3Rh(CO)H$, $[Rh(C_2H_4)_2Cl]_2$, $K_4Rh_2X_2(SnX_3)_4$ (wherein X represents Cl, Br or I)

$Rh[(n-C_4H_9)_3P]_2(CO)X$ (wherein X represents Br or I), $[(n-C_4H_9)_4N][Rh(CO)_2X_2]$ (wherein X represents Cl, Br or I), $[(n-C_4H_9)_4As]_2[Rh_2(CO)_2X_4]$ (wherein X represents Br or I), $[(n-C_4H_9)_4P][Rh(CO)I_4]$ and the like, and rhodium compounds described in Japanese Patent Publication-B No. 47-3334 (Jan. 29, 1972).

Examples of the palladium compounds suitable for use in the present invention include palladium chloride, palladium bromide, palladium iodide, palladium nitrate, palladium sulfate, palladium acetate, palladium propionate and palladium isobutyrate.

Examples of the palladium complexes suitable for use in the present invention include palladium acetylacetonate, sodium tetrachloropalladate, potassium tetrachloropalladate, potassium tetraiodopalladate, $[Pd(CO)Cl_2]_2$, $[(n-C_4H_9)_4P]_2(PdCl_4)$, $Pd[(C_6H_5)_3P]_2(CO)Br$, $Pd[(C_6H_5)_3P]_2I_2$ and $Pd[(n-C_4H_9)_3P]_2I_2$.

Examples of the molybdenum compounds suitable for use in the present invention include hexacarbonylmolybdenum, and examples of the nickel compounds include nickel iodide, nickel chloride and nickel acetate.

Optionally, the above catalysts may each further comprise a ligand such as an amine, phosphorus, a phosphine, an arsine, a stibine, etc.

The catalysts is used in a concentration thereof in the reaction fluid of generally 100 to 10,000 ppm, preferably 200 to 1,000 ppm.

The promoter is selected depending on the type of the catalyst. An example of the promoter includes methyl iodide. The promoter is used in an amount such that the concentration thereof in the reaction fluid is 5 to 20% by weight.

In the reaction fluid, in addition to the above components, water as a solvent is contained in an amount of from 0.1 to 15% by weight and acetic acid as a reaction product and as a solvent is contained as the main component, generally. This reaction is a continuous one, so that methyl acetate, which is produced by reacting methanol as a starting compound with acetic acid, is present in the reaction fluid in a range of from 0.1 to 30% by weight, generally in a range of from 0.5 to 30% by weight.

Further, according to necessity, a reaction accelerator is used. Examples of the reaction accelerator includes iodine compounds such as lithium iodide, sodium iodide, potassium iodide, rubidium iodide, cesium iodide, N-methylimidazole iodide and methyltributyl-phosphonium iodide, lithium compounds such as lithium acetate, Lewis acid metal compounds such as aluminum compounds and chromium compounds and amide compounds such as N-dimethylacetamide and N-methylpyrolidone. When a rhodium compound is used as the catalyst, the amount of the reaction accelerator to be added is generally from 5 to 400 times by mole, preferably 50 to 200 times by mole, as much as the rhodium present in the rhodium compound. When a rhodium compound and an aluminum compound are respectively used as the catalyst and the reaction accelerator, an excellent effect is attained by adding an aluminum compound in an amount of about 10 to 20 times by mole as much as the rhodium.

When an aluminum compound is used as the reaction accelerator, a boron compound may further be added to stabilize the reaction accelerator. Examples of the boron compound include boric acid and metaboric acid, which are each added in an amount of 1 to 10 times by mole as much as the aluminum present in the aluminum compound. Further, when an aluminum compound, a lithium compound or a Lewis acid metal compound is used as the reaction accelerator, an iodine compound may further be added to stabilize the reaction accelerator.

The reaction fluid is continuously withdrawn from the reactor (1), introduced into an evaporator (2) in which the pressure is controlled lower than the reaction pressure, and flash evaporation is conducted therein. The components evaporated in the evaporator are introduced into a distillation column (3), in which distillation is carried out. The components evaporated in the evaporator contain acetic acid.

In this distillation column (3), low boiling point components and high boiling point components are separated and removed. Namely, from the top of the distillation column (3), a distillate of low boiling point components (overhead) is obtained and introduced into a liquid separator (4), while high boiling point components are generally withdrawn from the bottom of the distillation column and recycled to the reactor (1). The distillate introduced into the liquid separator (4) is separated into two layers. The upper layer is an aqueous phase containing acetic acid and the lower layer is an organic phase containing acetic acid and methyl acetate (when methyl iodide is used as the promoter, the organic phase is mainly composed of methyl iodide). In these two phases, particularly in the aqueous phase as the upper layer, acetaldehydes are accumulated. These two phases are both recycled to the reactor (1).

A side stream containing acetic acid to become a product from the distillation column (3) is introduced into next distillation column (5). The distillation column (5) is also called a dehydrating tower. In the distillation column (5), dehydration is performed. The crude acetic acid thus obtained is withdrawn from the bottom of the column, and introduced into next distillation column (6). From the top of the distillation column (5), an overhead is separated and removed. This overhead is also recycled to the reactor (1) since it contains acetaldehyde.

In the distillation column (6) as well, distillation is performed, so that low boiling point components and high boiling point components are separated and removed. Specifically, in the distillation column (6), propionic acid as a high boiling point product and trace high boiling point impurities are withdrawn from the bottom, and low boiling point impurities are withdrawn from the top of the column. Acetic acid is obtained as a side cut from the distillation column (6). If desired, the distillation column (6) may be divided into a column for removing the high boiling point components and a column for removing the low boiling point components. Further purification of the acetic acid can also be attained thereby.

On the other hand, the offgas from the reactor (1) and the offgases (vented gases) from the evaporator (2) and the distillation columns (3) and (5) contain not only useful components but also trace impurities, such as acetaldehyde. The impurities, such as acetaldehyde, are not separated from organic components contained in the offgases, such as methyl iodide, but both are recovered by an absorption system (7) and recycled to the reactor (1).

If a practical continuous production of acetic acid is conducted according to the above Monsanto process for a prolonged period of time, trace impurities, i.e., acetaldehyde, unsaturated aldehydes (such as crotonaldehyde and 2-ethylcrotonaldehyde), saturated aldehydes and saturateed aliphatic carboxylic acids (e.g., propionic acid) formed by hydrogenation of such unsaturated aldehydes with the hydrogen present in the reaction fluid and methyl esters of saturated aliphatic carboxylic acids, accumulate in the reaction fluid.

Although the reaction for synthesizing acetic acid is effected while keeping the water concentration of the reaction fluid low under highly productive conditions disclosed in recent years, it is believed that the amount of by-products to be formed is decreased. However, in the reaction under the above conditions, the stability of the catalyst becomes poor. Consequently, for example, when a rhodium catalyst is employed, the reaction is preferably effected with a reaction fluid composition containing an iodide salt such as LiI and NaI in an amount of 1 to 10% by weight when the water content in the reaction fluid is from 5 to 10% by weight, or another reaction fluid composition containing an iodide salt in an amount of 10 to 20% by weight when the water content is 5% by weight or below.

The first embodiment of the present invention is characterized by adding, in the above process for producing acetic acid, a step of the treatment by which the concentration of unsaturated compounds in the crude acetic acid obtained by the process is to be 5 ppm or lower. The above treatment includes one for removing acetaldehyde from at least one process fluid separated in each step of the acetic acid producing process and recycled to the reactor. The method for separating and removing acetaldehyde from at least one process fluid mentioned above includes, for example, distillation of a process fluid containing acetaldehyde to separate acetaldehyde, extraction of acetaldehyde from a process fluid containing acetaldehyde, a combination of the above distillation and extraction, extractive distillation and the like.

As the process fluid from which acetaldehyde can be effectively separated by distillation, there can be mentioned the upper and lower layers in the liquid separator (4), the overhead from the distillation column (5) and a fluid in which organic substances contained in the offgases and recovered by the absorption system (7) are absorbed, by reason of their high acetaldehyde concentrations. Of these, the upper and lower layers in the liquid separator (4) are preferred as the fluid to be treated.

Methyl iodide used as the promoter is present in the above process fluids containing acetaldehyde. The boiling point of methyl iodide is close to that of acetaldehyde, so that their separation is one of the greatest difficulties. However, disposal of methyl iodide is difficult, because it is a compound containing iodine. Therefore, it is necessary either to separate and recover methyl iodide from the upper and lower layers in the liquid separator (4), then recycling the same to the reactor (1), or to separate and remove acetaldehyde from the upper and lower layers in the liquid separator (4), then recycling the remainder containing methyl iodide to the reactor (1).

The method for separating and removing acetaldehyde from the process fluid also includes a step wherein the process fluid containing acetaldehyde is distilled by a single distillation column. Preferably, however, it is accomplished by first separating low boiling point components composed of acetaldehyde and methyl iodide from other components by distillation, and subsequently performing a further distillation for separating methyl iodide and acetaldehyde from each other. Further, the separation and removal of acetaldehyde from the process fluid may also be performed by utilizing the properties that acetaldehyde is highly miscible with water while the miscibility of methyl iodide with water is poor. That is, the process fluid may be extracted with water to separate methyl iodide and aeetaldehyde, followed by distillation of the aqueous phase thus obtained.

In the first embodiment of the present invention, the amount of acetaldehyde which must be separated and removed from the reaction system in which acetic acid is synthesized, is such an amount that the total of unsaturated compounds (acetaldehyde derivatives) formed in the reaction system and contaminating the crude acetic acid in a continuous operation of the above acetic acid producing process, such as crotonaldehyde and 2-ethylcrotonaldehyde, becomes 5 ppm or lower. When the content of the above unsaturated compounds in the crude acetic acid is 5 ppm or lower, a highly purified acetic acid markedly improved in quality and exhibiting a long permanganate time can be obtained by ozonizing the crude acetic acid. On the other hand, from a crude acetic acid containing the unsaturated compounds in a concentration exceeding 5 ppm, a highly purified acetic acid cannot be obtained merely by ozonization thereof. Thus, further purification steps, such as distillation and separation must be effected. In this case, the ozonization means not only a futile treatment but also a waste of energy for purification.

As described above, the withdrawal of acetaldehyde from the acetic-acid producing process decreases not only the amount of trace, reducing impurities derived from acetaldehyde in the final acetic acid but also the amount of propionic acid to be formed as a by-product of the Monsanto process for producing acetic acid, so that, advantageously, the purification of the crude acetic acid is facilitated.

In the first embodiment of the present invention, acetaldehyde is withdrawn from the acetic acid producing process in the above manner and, further, the acetic acid obtained as a side stream from the last distillation column is ozonized, so that an acetic acid having a high quality from the viewpoint of the results of the reducing substance test is obtained. When the production of acetic acid is performed by a continuous operation, acetaldehyde is continuously formed. Thus, when the removal of acetaldehyde outside the system of the acetic acid producing process is effected by the above manner, the concentration of acetaldehyde in the reaction fluid does not become zero. On the other hand, the greater the amount of acetaldehyde withdrawn outside the system of the process, the smaller the concentration of acetaldehyde in the reaction or process fluid. In this case, the efficiency of removal of acetaldehyde from the process fluid is lowered. Thus, not only does the distillation equipment used for removing acetaldehyde from the process fluid become too large, but also the energy efficiency of distillation becomes poor.

Therefore, in the first embodiment of the present invention, the removal of acetaldehyde from the process fluid is restricted to an extent within which the removal can effectively be carried out. Namely, the concentration of unsaturated compounds in the crude acetic acid formed in the acetic acid producing process is not brought very close to zero but only reduced to a certain concentration (5 ppm) or lower, and, thereafter, the resultant crude acetic acid is ozonized. Thus, an acetic acid having a high quality is produced in a highly efficient manner.

The ozonization is performed at 40° C. or lower in order to avoid the danger of explosion. This also substantiates the effectiveness of the process of the present invention. That is, when the crude acetic acid or the process fluid in the step of producing acetic acid is ozonized, it is necessary to first cool the crude acetic acid or the process fluid, then ozonize the same and thereafter heat the ozonized acetic acid or process fluid for distillation. This is a thermally disadvantageous procedure. By contrast, the process of the present invention in which the ozonization is conducted as a final step, so that the acetic acid having undergone the ozonization, as it is, can be output as a product, is preferred because there is no waste of heat.

Ozone is generated by subjecting an air containing no excess water, an oxygen-enriched air which contains no excess water and has a high oxygen content or oxygen to vacuum discharge. The ozonization is performed by the use of a gas having an ozone concentration of 0.1 ppm or greater. Ozone rapidly decomposes in acetic acid. Thus, any ozone remaining in the final acetic acid product decomposes, if it is allowed to stand for a certain period of time after the ozonization. Hence, there is no problem in using excess ozone in the ozonization. However, it is essentially a wasted. Preferably, ozone is used in excess, in an amount of 1 to 3 times the molar concentration of impurities having unsaturated bonds, contained in the acetic acid.

The second embodiment of the present invention, it is characterized by continuously reacting methanol and/or an aqueous solution of methyl acetate with carbon monoxide in a reactor while maintaining the concentration of acetaldehyde in a reaction fluid in the reactor at 1500 ppm or lower. That is, in the second embodiment of the present invention, the amount of impurities to be formed is suppressed by maintaining the concentration of acetaldehyde in the reaction fluid at 1500 ppm or lower, preferably 1000 ppm or lower, in the practice of the above acetic acid producing process, preferably the acetic acid producing process under highly productive conditions. As a result, highly purified acetic acid can be produced merely by employing a fundamental simple distillation operation as a method for purifying the crude acetic acid.

For maintaining the concentration of acetaldehyde in the reaction fluid at 1500 ppm or lower, either the reaction conditions are controlled, or acetaldehyde is removed from the process fluid circulated in the process, i.e., recycled to the reactor for reutilization.

Among the reaction conditions, it was believed that the control of the partial pressure of hydrogen was most effective in maintaining the concentration of acetaldehyde in the reaction fluid at 1500 ppm or lower. More specifically, the present inventors believed that the amount of acetaldehyde to be formed would be decreased by decreasing the partial pressure of hydrogen, and that, as a result, the amount of propionic acid to be formed would be decreased. However, unexpectedly, it has become apparent that the decrease in the partial pressure of hydrogen would deprive the reducing unsaturated compounds, extremely detrimental to the results of the reducing substance test for acetic acid, such as crotonaldehyde and 2-ethylcrotonaldehyde, of their opportunities of being converted to saturated compounds (rendered harmless) by hydrogenation. That is, it has occurred that the decrease in the partial pressure of hydrogen during the reaction rather causes the quality of acetic acid, especially the permanganate time, to be poor, so that only acetic acid having a low purity can be obtained. Therefore, it has been found that, for maintaining the concentration of acetaldehyde in the reaction fluid at 1500 ppm or lower, it is preferred to remove acetaldehyde from the process fluid recycled to the reactor for reutilization.

The method for separating and removing acetaldehyde from the process fluid containing acetaldehyde and the process fluid from which acetaldehyde can effectively be separated and removed, are as described with respect to the first embodiment of the present invention.

In the second embodiment of the present invention, the amount of acetaldehyde which must be separated and removed from the acetic acid producing process is such an amount that the concentration of acetaldehyde in the reaction fluid in a continuous steady-state reaction is maintained at 1500 ppm or lower, preferably 1000 ppm or lower.

In the first embodiment of the present invention, acetaldehyde is separated and removed by distillation or any other method from the low boiling point process fluid containing acetaldehyde, recycled for reutilization to the reactor in the process for continuously producing acetic acid, and the crude acetic acid is ozonized. As a result, acetic acid having a desirably high quality, i.e., exhibiting a long permanganate time, can be produced merely by the execution of conventional purification without the need for enormous equipment and wasted of energy, according to the first embodiment of the present invention.

In the second embodiment of the present invention, the reaction is carried out while maintaining the concentration of acetaldehyde in the reaction fluid to 1500 ppm or lower by separating and removing acetaldehyde by distillation or other methods from the low boiling point process fluid containing acetaldehyde, recycled for reutilization to the reactor in the process for continuously producing acetic acid. As a result, acetic acid having a desirably high quality, i.e., exhibiting a long permanganate time, can be produced merely by the execution of conventional purification without the need for enormous equipment and waste of energy and without the need for the ozonization step, according to the second embodiment of the present invention. Moreover, by virtue of the second embodiment of the present invention, not only is the amount of trace, reducing impurities derived from acetaldehyde in the final acetic acid lowered but also the amount of propionic acid to be formed as a by-product of the Monsanto process for producing acetic acid is lowered, so that the purification of acetic acid is facilitated also from this point of view.

EXAMPLES

The present invention will now be described in greater detail with reference to the following Examples, which should not be construed as limiting the scope of the present invention.

Example 1

This example demonstrates that it is possible to distill off acetaldehyde.

A model fluid of the upper layer fluid in the liquid separator in the process for producing acetic acid, which contained 1% by weight of acetaldehyde, was prepared. This model fluid was distilled by the use of a 30-plate Oldershaw distillation column having an inside diameter of 40 mm under the following conditions:

composition of model fluid;

| | |
|---|---|
| methyl iodide | 7% by weight |
| acetic acid | 44% by weight |
| water | 48% by weight |
| acetaldehyde | 1.0% by weight, and distillation conditions; |
| reflux ratio | 1.5 |
| amount of withdrawn fluid | 8.5 parts from top of column and 91.5 parts from bottom of column per 100 parts of feed, |
| plate at which fluid was fed | 17th plate from top. |

The distillate from the top of the distillation column contained the whole of the feed acetaldehyde and most of the feed methyl iodide. The composition of the distillate was as follows:

| | |
|---|---|
| methyl iodide | 82.3% by weight |
| water | 5.9% by weight |
| acetaldehyde | 11.8% by weight. |

The above distillate was distilled by the use of a 60-plate distillation column having an inside diameter of 40 mm under the following conditions. Acetaldehyde flowed out of the top of the distillation column to be separated from methyl iodide. distillation conditions;

| | |
|---|---|
| plate at which fluid was fed | 57th plate from top |
| reflux ratio | 150 |
| amount of withdrawn fluid | 11 parts from top of column and 89 parts from bottom of column per 100 parts of feed, and composition of overhead; |
| acetaldehyde | 99.99% by weight |
| methyl iodide | up to 100 ppm. |

Example 2

This example also demonstrates that it is possible to distill off acetaldehyde.

As in Example 1, a model fluid of the lower layer fluid in the liquid separator in the process for producing acetic acid, which contained 0.4% by weight of acetaldehyde, was prepared. This model fluid was distilled by the use of a 30-plate Oldershaw distillation column having an inside diameter of 40 mm under the following conditions:

composition of model fluid;

| | |
|---|---|
| methyl iodide | 90.2% by weight |
| methyl acetate | 5.0% by weight |
| acetic acid | 3.5% by weight |
| water | 0.9% by weight |
| acetaldehyde | 0.4% by weight, and distillation conditions; |
| reflux ratio | 3.0 |
| amount of withdrawn fluid | 94 parts from top of column and 6 parts from bottom of column per 100 parts of feed |
| plate at which fluid was fed | 17th plate from top. |

The distillate from the top of the distillation column contained the whole of the feed acetaldehyde and most of the feed methyl iodide. The composition of the distillate was as follows:

| | |
|---|---|
| methyl iodide | 93.3% by weight |
| methyl acetate | 5.3% by weight |
| water | 0.96% by weight |
| acetaldehyde | 0.43% by weight. |

The above distillate was distilled by the use of a 60-plate distillation column having an inside diameter of 40 mm under the following conditions. Acetaldehyde flowed out of the top of the distillation column to be separated from methyl iodide. distillation conditions;

| | | 57th plate from top |
|---|---|---|
| plate at which fluid was fed | | 57th plate from top |
| reflux ratio | | 150 |
| amount of withdrawn fluid | | 0.28 part from top of column per 100 parts of feed, and composition of overhead; |
| acetaldehyde (corresponding to about 70% by weight of the amount of the feed acetaldehyde) | | 99.99% by weight |
| methyl iodide | | up to 100 ppm. |

Example 3

This example demonstrates the effectiveness of ozonization.

A product acetic acid which contained crotonaldehyde and 2-ethylcrotonaldehyde as impurities in a total amount of 2.8 ppm and exhibited a permanganate time of 150 min was treated with air containing 20 ppm of ozone. The ozonization was continuously conducted, specially by flowing the acetic acid at a flow rate of 0.1 l/hr into continuous contact at 25° C. with the air containing 20 ppm of ozone flowing at a flow rate of 10 l/hr. After the ozonization, the acetic acid exhibited a permanganate time of 300 min. The crotonaldehyde and 2-ethylcrotonaldehyde were almost completely decomposed by the ozonization.

Comparative Example 1

This example demonstrate that acetic acid having a high quality is not always produced only by ozonization.

A product acetic acid which contained crotonaldehyde and 2-ethylcrotonaldehyde as impurities in a total amount of 8.2 ppm and exhibited a permanganate time of 30 min was treated with air containing 40 ppm of ozone. The ozonization was continuously conducted, specially by flowing the acetic acid at a flow rate of 0.1 l/hr into continuous contact at 25° C. with the air containing 40 ppm of ozone flowing at a flow rate of 10 l/hr. The above amount of ozone was greater than that required to completely decompose (completely hydrogenate) the unsaturated compounds in the acetic acid. After the ozonization, the acetic acid exhibited a-permanganate time of 100 min. The crotonaldehyde and 2-ethylcrotonaldehyde were almost completely decomposed by the ozonization, so that these compounds were not detected in the acetic acid. However, the contents of acetaldehyde and formaldehyde in the acetic acid were increased. Namely, the cause wherein the permanganate time was not improved was the formation of these reducing compounds.

Example 4

Model fluids for low-quality acetic acid were prepared by adding given amounts of crotonaldehyde and 2-ethylcrotonaldehyde, respectively to highly purified acetic acids, each exhibiting a permanganate time of 240 min, and their permanganate times were measured. Further, each of the model fluids was contacted with a dry air containing 10 ppm of ozone (this amount of ozone corresponded to 50 ppm of acetic acid) to conduct ozonization. After the ozonization, the model fluids were allowed to stand for one day, and were each subjected to the permanganate reducing substance test. Thus, results as shown in Table 1 were obtained. The results demonstrated that the acetic acids, each containing an unsaturated compound in an amount exceeding 5 ppm, were not completely converted to highly purified acetic acids, even after the ozonization.

TABLE 1

| additive | amount of addition (ppm) | permanganate time (min.) prior to ozonization | permanganate time (min.) after ozonization |
|---|---|---|---|
| none (highly purified acetic acid) | 0 | 240 | 300 |
| crotonaldehyde | 2 | 80 | 180 |
| | 5 | 20 | 120 |
| | 10 | 3 | 90 |
| 2-ethylcrotonaldehyde | 2 | 150 | 230 |
| | 5 | 80 | 135 |
| | 10 | 45 | 100 |

Example 5

One mode of the process for producing acetic acid with the use of a continuously operated pilot plant as illustrated in FIG. 1 will be described as an example.

The outline of this mode of process employed is as follows.

Methanol and carbon monoxide as starting compounds are continuously fed to a reactor (1) and continuously reacted at a temperature of from 187° to 189° C. under a pressure of 28 kg/cm². The reaction fluid is continuously withdrawn from the reactor (1), and introduced into an evaporator (2) in which the pressure is lower than the reaction pressure. Flash evaporation is conducted therein. Components evaporated in the evaporator (2) are introduced into a distillation column (3), in which distillation is performed. The overhead from the top of the distillation column is introduced into a liquid separator (4), and separated into two phases therein. The upper layer is an aqueous phase containing acetic acid, and the lower layer is an organic phase (methyl iodide phase) containing acetic acid and water. In these two phases, acetaldehyde is concentrated. Especially in the upper layer, acetaldehyde is concentrated. These two phases are recycled to the reactor (1). Of them, the upper layer is distilled as will be described hereinbelow and then is recycled to the reactor (1). High boiling point components from the distillation column (3) are also recycled to the reactor (1). A side stream from the distillation column (3), containing acetic acid to be a product, is introduced into the next distillation column (5). Crude acetic acid obtained by dehydration in the distillation column (5) is withdrawn from the bottom of the distillation column (5), and introduced into the next distillation column (6), in which distillation is performed. The overhead from the distillation column (5) is also recycled to the reactor (1) although it also contains acetaldehyde. In the distillation column (6), propionic acid as a high boiling point product and a trace of high boiling point impurities are withdrawn from the bottom of the column, and low boiling point impurities are withdrawn from the top of the column. A desired crude acetic acid is obtained as a side stream from the distillation column (6). On the other hand, although acetaldehyde is contained in the offgas from the reactor (1) and in the offgases from the evaporator (2) and from the distillation columns (3) and (5), the acetaldehyde is recovered by an absorption system (7) together with organic components such as methyl iodide, and recycled to the reactor (1).

Under the above production conditions, the upper layer fluid in the liquid separator (4), which was composed of 0.5% by weight of acetaldehyde, water, acetic acid, methyl iodide and methyl acetate, was withdrawn at a rate of 0.25 l/hr (the quantity being ½ of the total of the upper layer fluid), and continuously distilled in a 40-plate distillation column a having an inside diameter of 60 mm under a pressure of 1.2 kg/cm². The feed was effected at the 20th plate from the top of the column. The reflux ratio of the overhead was 3.0. The fluid was withdrawn from the bottom of the distillation column a at a rate of 0.24 l/hr, and recycled to the reactor (1). On the other hand, the overhead mainly composed of methyl iodide and acetaldehyde was withdrawn at a rate of 0.015 l/hr from the top of the distillation column a. The withdrawn overhead was fed into a 60-plate distillation column L having an inside diameter of 50 mm at its 57th plate, and distilled at a reflux ratio of 40 under a pressure of 1.0 kg/cm². From the top of the distillation column b, acetaldehyde was isolated at a rate of 0.8 g per hour. On the other hand, the fluid was withdrawn at a rate of 0.015 l/hr from the bottom of the distillation column b, and recycled to the reactor (1). The permanganate time of the crude acetic acid obtained in this process, i.e., the acetic acid obtained as the side cut from the distillation column (6), was 120 min. The crude acetic acid obtained in this process contained crotonaldehyde and 2-ethylcrotonaldehyde in a total amount of 4.3 ppm.

Subsequently, this crude acetic acid was treated in an ozonizing vessel. Namely, the crude acetic acid was flowed at a flow rate of 0.1 kg/hr, while a dry air containing 20 ppm of ozone was blown thereinto at 25° C. at a flow rate of 10 l/hr. After the ozonization, the permanganate time of the acetic acid was 300 min. The total concentration of crotonaldehyde and 2-ethylcrotonaldehyde in this acetic acid had decreased to 0.1 ppm or lower.

Example 6

One mode of the process for producing acetic acid with the use of a continuously operated pilot plant as illustrated in FIG. 1 will be described as an example.

The outline of this mode of process employed is as follows.

Methanol and carbon monoxide as starting compounds are continuously fed to a reactor (1) containing a catalyst and other components were fed in such amounts that the concentrations, which are described as concentrations in reaction fluid at steady state, of rhodium, methyl iodide, lithium iodide, water and methyl acetate become 450 ppm, 13% by weight, 4.5% by weight, 8% by weight and 1.2% by weight, respectively, and continuously reacted at a temperature of from 187° to 189° C. under a pressure of 28 kg/cm² and a partial pressure of hydrogen of 1.2 kg/cm². The reaction fluid is continuously withdrawn from the reactor (1), and introduced into an evaporator (2) in which the pressure is lower than the reaction pressure. Flash evaporation is conducted therein. Components evaporated in the evaporator (2) are introduced into a distillation column (3), in which distillation is performed. Low boiling point components are mainly separated in this distillation column (3). The overhead from the top of the distillation column is introduced into a liquid separator (4), and separated into two phases therein. The upper layer is an aqueous phase containing acetic acid, and the lower layer is an organic phase (methyl iodide phase) containing acetic acid and methyl acetate. Especially in the upper layer, acetaldehyde is concentrated. These two phases are recycled to the reactor (1). Of them, the upper layer is distilled as will be described hereinbelow and then is recycled to the reactor (1). High boiling point components from the distillation column (3) are also recycled to the reactor (1). A side stream from the distillation column (3), containing acetic acid to be a product, is introduced into the next distillation column (5). Crude acetic acid obtained by dehydration in the distillation column (5) is withdrawn from the bottom of the distillation column (5), and introduced into the next distillation column (6), in which distillation is performed. The overhead from the distillation column (5) is also recycled to the reactor (1) although it also contains acetaldehyde. In the distillation column (6), propionic acid as a high boiling point product and a trace of high boiling point impurities are withdrawn from the bottom of the column, and low boiling point impurities are withdrawn from the top of the column. A desired crude acetic acid is obtained as a side stream from the distillation column (6). On the other hand, although acetaldehyde is contained in the offgas from the reactor (1) and in the off gases from the evaporator (2) and from the distillation columns (3) and (5), the acetaldehyde is recovered by an absorption system (7) together with organic components such as methyl iodide, and recycled to the reactor (1).

According to the above process, continuous reaction was carried out by the pilot plant which had a capacity for producing 5 kg of acetic acid per hour. Under the above production conditions, the upper layer fluid in the liquid separator (4), which was composed of 0.5% by weight of acetaldehyde, water, acetic acid, methyl iodide and methyl acetate, was withdrawn at a rate of 0.25 l/hr (the quantity being ⅓ of the total of the upper layer fluid), and continuously distilled in a 40-plate distillation column a having an inside diameter of 60 mm under a pressure of 1.2 kg/cm². The feed was effected at the 20th plate from the top of the column. The reflux ratio of the overhead was 3.0. The fluid was withdrawn from the bottom of the distillation column a at a rate of 0.24 l/hr, and recycled to the reactor (1). On the other hand, the overhead mainly composed of methyl iodide and acetaldehyde was withdrawn at a rate of 0.015 l/hr from the top of the distillation column a. The withdrawn overhead was fed into a 60-plate distillation column b having an inside diameter of 50 mm at its 57th plate, and distilled at a reflux ratio of 40 under a pressure of 1.0 kg/cm². From the top of the distillation column b, acetaldehyde was isolated at a rate of 0.8 g per hour. On the other hand, the fluid was withdrawn at a rate of 0.015 l/hr from the bottom of the distillation column b, and recycled to the reactor (1).

The permanganate time of the crude acetic acid obtained in this process, i.e., the acetic acid obtained as the side stream the distillation column (6), was 150 min. The crude acetic acid obtained in this process contained crotonaldehyde and 2-ethylcrotonaldehyde in a total amount of 4.0 ppm. In this acetic acid production process, the concentration of acetaldehyde in the reaction fluid in the reactor (1) was maintained at 800 to 1000 ppm.

Subsequently, this crude acetic acid was treated in an ozonizing vessel. Namely, the crude acetic acid was flowed at a flow rate of 0.1 kg/hr, while a dry air containing 20 ppm of ozone was blown thereinto at 25° C. at a flow rate of 10 l/hr. After the ozonization, the permanganate time of the acetic acid was 300 min. The total concentration of crotonaldehyde and 2-ethylcrotonaldehyde in this acetic acid had been decreased to 0.1 ppm or lower.

Comparative Example 2

Continuous pilot production of acetic acid [up to the step of the side stream the distillation column (6)] was performed according to the same process and under the same conditions as those of Example 5, except that the removal (distillation operation) of acetaldehyde from the upper layer fluid in the liquid separator (4) was not carried out.

The permanganate time of the thus obtained crude acetic acid [side cut from the distillation column (6)] was 60 min. The crude acetic acid contained crotonaldehyde and 2-ethylcrotonaldehyde in a total amount of 7.5 ppm. In this acetic acid production process, the concentration of acetaldehyde in the reaction fluid in the reactor (1) was from 1700 to 1800 ppm.

Then, the crude acetic acid thus obtained was treated in an ozonizing vessel. Namely, this crude acetic acid was flowed at a flow rate of 0.1 kg/hr, while a dry air containing 40 ppm of ozone was blown thereinto at 25° C. at a flow rate of 10 l/hr. The total concentration of crotonaldehyde and 2-ethylcrotonaldehyde in the resultant acetic acid decreased to 0.1 ppm or lower. However, the permanganate time thereof was 100 min.

Comparative Example 3

Continuous pilot production of acetic acid [up to the step of the side cut from the distillation column (6)] was performed according to the same process and under the same conditions as those of Example 5, except that methanol and carbon monoxide as starting compounds were continuously fed to the reactor (1) and continuously reacted at a temperature of 187° C., under a pressure of 28 kg/cm$^2$ and a partial pressure of hydrogen of 0.9 kg/cm$^2$, and that the amount of rhodium fed into the reactor (1) was 400 ppm.

The concentrations of unsaturated compounds in the thus obtained crude acetic acid [stream from the distillation column (6)] was as follows:

| | |
|---|---|
| crotonaldehyde | 1.7 ppm, and |
| 2-ethylcrotonaldehyde | 3.4 ppm. |

The permanganate time of this crude acetic acid was 50 min.

This acetic acid was treated in an ozonizing vessel. Namely, this crude acetic acid was flowed at a flow rate of 0.1 kg/hr, while dry air containing 20 ppm of ozone was blown thereinto at 25° C. at a flow rate of 10 l/hr. The total concentration of crotonaldehyde and 2-ethylcrotonaldehyde in the resultant acetic acid had decreased to 0.1 ppm or lower. However, the permanganate time thereof was 110 min.

Example 7

Continuous pilot production of acetic acid [up to the step of the side stream from the distillation column (6)] was performed according to the same process and under the same conditions as those of Example 6, except that methanol and carbon monoxide as starting compounds were continuously fed to the reactor (1) and continuously reacted at a temperature of 187° C., under a pressure of 28 kg/cm$^2$ and a partial pressure of hydrogen of 2.4 kg/cm$^2$, and that the amount of rhodium fed into the reactor (1) was 400 ppm.

The concentrations of unsaturated compounds in the thus obtained crude acetic acid [side stream from the distillation column (6)] was as follows:

| | |
|---|---|
| crotonaldehyde | 0.8 ppm, and |
| 2-ethylcrotonaldehyde | 1.8 ppm. |

The permanganate time of this crude acetic acid was 125 min.

This acetic acid was treated in an ozonizing vessel. Namely, this crude acetic acid was flowed at a flow rate of 0.1 kg/hr, while dry air containing 10 ppm of ozone was blown thereinto at 25° C. at a flow rate of 10 l/hr. The permanganate time of the resultant acetic acid was 230 min. The total concentration of crotonaldehyde and 2-ethylcrotonaldehyde therein had decreased to 0.1 ppm or lower.

Example 8

One mode of the process for producing acetic acid with the use of a continuously operated pilot plant as illustrated in FIG. 1 will be described as an example.

The outline of this mode of process employed is as follows.

Methanol and carbon monoxide as starting compounds are continuously fed to a reactor (1) containing a catalyst and others fed in such amounts that the concentrations, which are described as concentrations in reaction fluid at steady state, of rhodium, methyl iodide, lithium iodide, water and methyl acetate become 450 ppm, 13% by weight, 4.5% by weight, 8% by weight and 1.2% by weight, respectively, and continuously reacted at a temperature of from 187° to 189° C. under a pressure of 28 kg/cm$^2$. The reaction fluid is continuously withdrawn from the reactor (1), and introduced into an evaporator (2) in which the pressure is lower than the reaction pressure. Flash evaporation is conducted therein. Components evaporated in the evaporator (2) are introduced into a distillation column (3), in which distillation is performed. Low boiling point components are mainly separated in this distillation column (3). The overhead from the top of the distillation column is introduced into a liquid separator (4), and separated into two phases therein. Of them, the upper layer is distilled as will be described hereinbelow before being recycled to the reactor (1). High boiling point components from the distillation column (3) are also recycled to the reactor (1). A side stream from the distillation column (3), containing acetic acid to be a product, is introduced into the next distillation column (5). Crude acetic acid obtained by dehydration in the distillation column (5) is withdrawn from the bottom of the distillation column (5), and introduced into the next distillation column (6), in which distillation is performed. In the distillation column (6), propionic acid as a high boiling point product and a trace of high boiling point impurities are withdrawn from the bottom of the column, and low boiling point impurities are withdrawn from the top of the column. A desired crude-acetic acid is obtained as a side stream from the distillation column (6). On the other hand, although acetaldehyde is contained in the offgas from the reactor (1) and in the offgases from the evaporator (2) and from the distillation columns (3) and (5), the acetaldehyde is recovered by an absorption system (7) together with organic components such as methyl iodide, and recycled to the reactor (1).

According to the above process, continuous reaction was carried out to produce acetic acid. During the continuous reaction, the concentration of acetaldehyde in the reaction fluid in the reactor (1) was controlled to be 800 to 1000 ppm by conducting the following operation.

Under the above production conditions, the upper layer fluid in the liquid separator (4), which was composed of 0.5% by weight of acetaldehyde, water, acetic acid, methyl iodide and methyl acetate, was withdrawn at a rate of 0.25 l/hr (the quantity being ⅓ of the total of the upper layer fluid), and continuously distilled in a 40-plate distillation column a having an inside diameter of 60 mm under a pressure of 1.2 kg/cm². The feed was effected at the 20th plate from the top of the column. The reflux ratio of the overhead was 3.0. The fluid was withdrawn from the bottom of the distillation column a at a rate of 0.24 l/hr, and recycled to the reactor (1). On the other hand, the overhead mainly composed of methyl iodide and acetaldehyde was withdrawn at a rate of 0.015 l/hr from the top of the distillation column a. The withdrawn overhead was fed into a 60-plate distillation column b having an inside diameter of 50 mm at its 57th plate, and distilled at a reflux ratio of 40 under a pressure of 1.0 kg/cm². From the top of the distillation column b, acetaldehyde was isolated at a rate of 0.8 g per hour. On the other hand, the fluid was withdrawn at a rate of 0.015 l/hr from the bottom of the distillation column A, and recycled to the reactor (1).

The permanganate time of the crude acetic acid obtained in this process, i.e., the acetic acid obtained as the side stream from the distillation column (6), was 240 min. The concentration of acetaldehyde in the reaction fluid was maintained at 800 to 1000 ppm as described above.

Comparative Example 4

Continuous pilot production of acetic acid [up to the step of the side stream from the distillation column (6)] was performed according to the same process and under the same conditions as-those of Example 8, except that the removal (distillation operation) of acetaldehyde from the upper layer fluid in the liquid separator (4) was not carried out. In this pilot production, the concentration of acetaldehyde in the reaction fluid reached a steady state at 1700 to 1800 ppm. The permanganate time of the crude acetic acid [side stream from the distillation column (6)] obtained when the acetaldehyde concentration was in the steady state was 60 min.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. In a process for producing a highly purified acetic acid in which methanol and/or an aqueous solution of methyl acetate is reacted with carbon monoxide in the presence of a rhodium complex and methyl iodide in a reaction system, the improvement comprising conducting said reaction at a water content not greater than 10 wt. % and an acetaldehyde concentration of not greater than 1500 ppm to produce a crude acetic acid product mixture; sending the crude acetic acid product mixture to a distillation column to produce a high-boiling point fraction and a low-boiling point fraction; treating the low-boiling point fraction to reduce the content of acetaldehyde therein; and returning the treated low-boiling point fraction to the reaction system.

2. The process for producing a highly purified acetic acid according to claim 1, wherein said treatment for removing acetaldehyde is either distillation and/or extraction or extractive distillation of the process fluid.

3. The process for producing a highly purified acetic acid according to claim 1, wherein acetaldehyde is removed from at least one process fluid separated in each step of the process and recycled to the reactor to maintain the concentration of acetaldehyde in a reaction fluid in the reactor at 1500 ppm or lower.

4. The process for producing a highly purified acetic acid according to claim 3, wherein said treatment for removing acetaldehyde is either distillation and/or extraction or extractive distillation of the process fluid.

5. The process for producing a highly purified acetic acid according to claim 1, wherein said water content is from 5 to 10 wt. %.

6. The process for producing a highly purified acetic acid according to claim 1, wherein said water content is not greater than 5 wt. %.

7. The process for producing a highly purified acetic acid according to claim 1, wherein the low-boiling point fraction is treated in a separator where an upper layer and lower layer is formed and the upper layer is distilled to remove acetaldehyde therefrom.

8. The process for producing a highly purified acetic acid according to claim 1, wherein the low-boiling point fraction contains methyl iodide, methyl acetate and acetaldehyde.

9. In a process for producing a highly purified acetic acid in which methanol and/or an aqueous solution of methyl acetate is reacted with carbon monoxide in the presence of a rhodium complex and methyl iodide, the improvement comprising conducting said reaction at a water content of not greater than 10 wt. % to obtain a crude acetic acid product mixture, treating the crude acetic acid product mixture so that it contains no more than 5 ppm of unsaturated compounds by removing acetaldehyde from at least one process fluid containing acetaldehyde and methyl iodide separated in each step of the process and recycled to the process and ozonizing the treated crude acetic acid product mixture to obtain highly purified acetic acid.

10. The process for producing a highly purified acetic acid according to claim 1, wherein the adjustment of the water content to not greater than 10 wt. % and the aldehyde concentration to not greater than 1500 ppm are effected in a reactor.

11. The process for producing a highly purified acetic acid according to claim 11, wherein the acetaldehyde concentration is not greater than 1,000 ppm.

* * * * *

UNITED STATES PATENT AND TRADEMARK OFFICE
CERTIFICATE OF CORRECTION

PATENT NO. : 5,756,836
DATED : May 26, 1998
INVENTOR(S) : Masahiko SHIMIZU et al It is certified that error appears in the above-indentified patent and that said Letters Patent is hereby corrected as shown below:

Column 20, line 53; change "claim 11" to ---claim 1 --.

Signed and Sealed this

Twenty-fourth Day of November,1998

Attest:

BRUCE LEHMAN

*Attesting Officer*  *Commissioner of Patents and Trademarks*